United States Patent [19]

Alker et al.

[11] Patent Number: 4,654,353

[45] Date of Patent: Mar. 31, 1987

[54] ANTIHYPERTENSIVE 2-HYDROXYALKOXYALKYL DIHYDROPYRIDINES

[75] Inventors: David Alker, Eastry; Simon F. Campbell, Kingsdown, Deal; Peter E. Cross, Canterbury, all of England

[73] Assignee: Pfizer Inc., New York, N.Y.

[21] Appl. No.: 727,704

[22] Filed: Apr. 26, 1985

[30] Foreign Application Priority Data

May 12, 1984 [GB] United Kingdom ................. 8412208

[51] Int. Cl.$^4$ .................. C07D 211/90; C07D 401/04; A61K 31/455
[52] U.S. Cl. ..................................... 514/334; 514/356; 546/258; 546/321; 546/271; 546/283; 546/167; 544/333
[58] Field of Search ................ 546/321, 258; 514/356, 514/334

[56] References Cited

U.S. PATENT DOCUMENTS 4,430,333 2/1984 Campbell et al. .................... 424/266
4,532,248 7/1985 Franckowiak et al. ............. 546/310

FOREIGN PATENT DOCUMENTS 0031801 7/1981 European Pat. Off. .
100189 2/1984 European Pat. Off. .

Primary Examiner—Henry R. Jiles
Assistant Examiner—Dale A. Bjorkman
Attorney, Agent, or Firm—Charles J. Knuth; Albert E. Frost; James M. McManus

[57] ABSTRACT

Compounds of the formula:

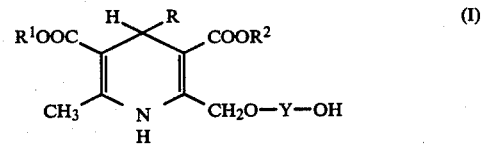

where
R is an optionally substituted aryl or heteroaryl group;
$R^1$ and $R^2$ are each independently $C_1$-$C_4$ alkyl or 2-methoxyethyl; and Y is —$(CH_2)_n$— where n is 2, 3 or 4, —$CH_2CH(CH_3)$— or —$Ch_2C(CH_3)_2$—; and their pharmaceutically acceptable salts.

The compounds have utility as anti-ischaemic and antihypertensive agents and as synthetic intermediates to other dihydropyridine calcium antagonists.

7 Claims, No Drawings

ANTIHYPERTENSIVE 2-HYDROXYALKOXYALKYL DIHYDROPYRIDINES

BACKGROUND OF THE INVENTION

This invention relates to certain dihydropyridines, specifically to certain 1,4-dihydropyridines having a hydroxy or oxo substituent in a side chain attached to the 2-position, which have utility as anti-ischaemic and antihypertensive agents and also as synthetic intermediates.

The compounds of the invention reduce the movement of calcium into the cell and they are thus able to delay or prevent the cardiac contracture which is believed to be caused by an accumulation of intracellular calcium under ischaemic conditions. Excessive calcium influx during ischaemia can have a number of additional adverse effects which would further compromise the ischaemic myocardium. These include less efficient use of oxygen for ATP production, activation of mitochondrial fatty acid oxidation and possibly, promotion of cell necrosis. Thus the compounds are useful in the treatment or prevention of a variety of cardiac conditions, such as angina pectoris, cardiac arrhythmias, heart attacks and cardiac hypertrophy. The compounds also have vasodilator activity since they can inhibit calcium influx in cells of vascular tissue and they are thus also useful as antihypertensive agents and for the treatment of coronary vasospasm.

SUMMARY OF THE INVENTION

According to the invention, there are provided novel 1,4-dihydropyridine derivatives of the formula:

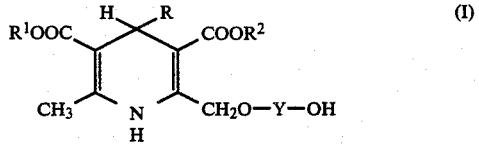

(I)

where
R is an optionally substituted aryl or heteroaryl group;
$R^1$ and $R^2$ are each independently $C_1$–$C_4$ alkyl or 2-methoxyethyl; and
Y is —$(CH_2)_n$— where n is 2,3 or 4, —$CH_2CH(CH_3)$— or —$CH_2C(CH_3)_2$—;
and their pharmaceutically acceptable salts.

The term "aryl" as used in this specification includes unsubstituted phenyl and phenyl substituted by, for example, one or two substituents each independently selected from nitro, halo, $C_1$–$C_4$ alkyl, $C_1$–$C_4$ alkoxy, hydroxy, trifluoromethyl, and cyano. It also includes 1- and 2-naphthyl.

"Halo" means F, Cl, Br or I.

The term "heteroaryl" as used in this specification for R means an aromatic heterocyclic group which may optionally be substituted and includes, for example, benzofuranyl; benzothienyl; pyridyl optionally monosubstituted by methyl, thiomethyl, halo or cyano; quinolyl; benzoxazolyl; benzthiazolyl; furyl; pyrimidinyl; thiazolyl; 2,1,3-benzoxadiazol-4-yl; 2,1,3-benzthiadiazol-4-yl; and thienyl optionally monosubstituted by halo or $C_1$–$C_4$ alkyl.

Alkyl and alkoxy groups having 3 or more carbon atoms can be straight or branched chain.

R is preferably phenyl substituted by 1 or 2 substituents selected from halo and $CF_3$, or is 2-chloropyrid-3-yl. R is most preferably 2-chlorophenyl, 2,3-dichlorophenyl, 2-chloro-3-trifluoromethylphenyl or 2-chloropyrid-3-yl.

Preferably either $R^1$ is $CH_3$ and $R^2$ is $C_2H_5$ or $R^1$ is $C_2H_5$ and $R^2$ is $CH_3$. Most preferably, $R^1$ is $CH_3$ and $R^2$ is $C_2H_5$.

Y is preferably —$(CH_2)_2$—, —$(CH_2)_4$—, —$CH_2CH(CH_3)$— or —$CH_2C(CH_3)_2$—.

The compounds of the formula (I) containing one or more asymmetric centres will exist as one or more pairs of enantiomers, and such pairs or individual isomers may be separable by physical methods, e.g. by fractional crystallisation or chromatography of the parent compounds or suitable derivatives thereof as will be known to those skilled in the art. The invention includes the separated pairs as well as mixtures thereof, as racemic mixtures or as separated optically-active isomeric forms.

DETAILED DESCRIPTION OF THE INVENTION

The compounds of the invention can be prepared by a number of routes, including the following:

(1) Compounds of the formula (I) in which Y is —$(CH_2)_2$— can be prepared as follows:

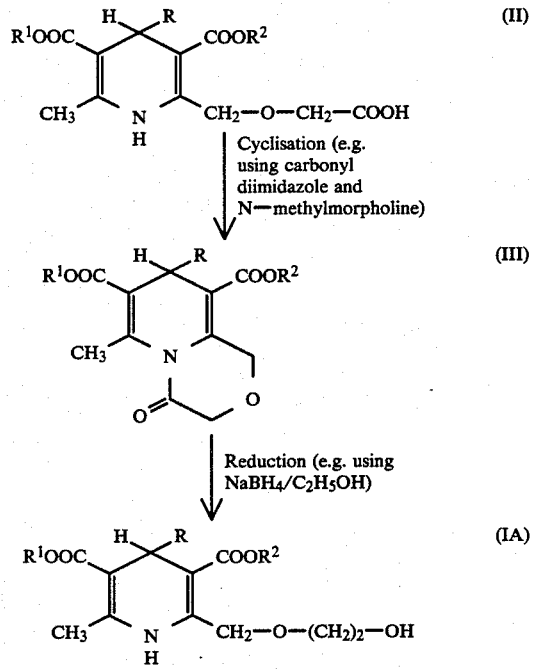

The cyclisation is typically carried out by stirring the dihydropyridine (II), carbonyl diimidazole and N-methylmorpholine in a suitable organic solvent, e.g. tetrahydrofuran, until the reaction is complete. The product (III) can then be recovered by conventional means. The reduction can then be carried out by reducing the oxazine (III) with a suitable reducing agent in an organic solvent, e.g. sodium borohydride in ethanol at room temperature, or lithium aluminium hydride in tetrahydrofuran at about 0° C. If necessary, the reaction mixture can be heated at up to 80° C. to accelerate the reaction. The product can again be isolated and purified conventionally.

The intermediates of the formula (III) also form a part of this invention.

The starting materials of the formula (II) are either known compounds or can be prepared analogously to the prior art, see e.g. European patent application publication No. 0100189. A typical procedure is as follows:

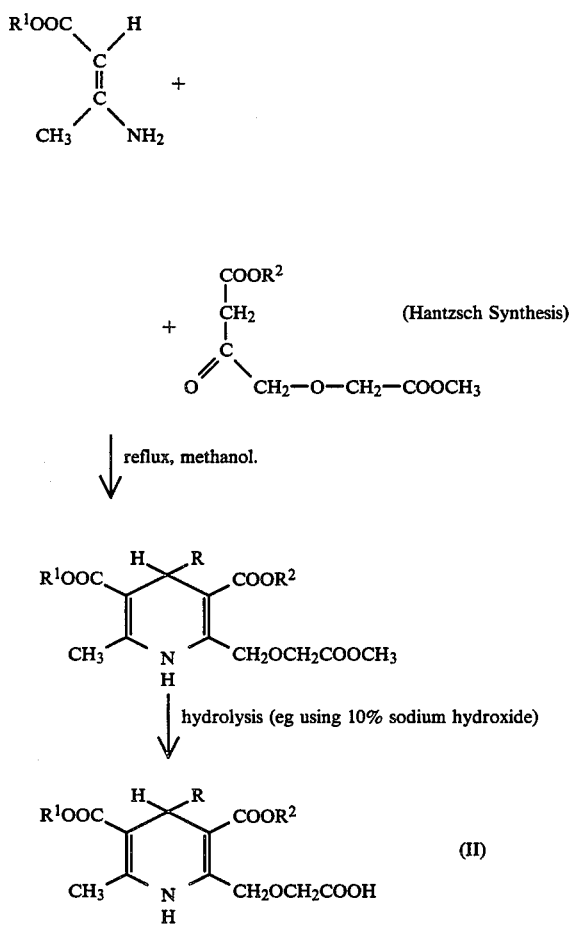

(2) Compounds in which Y is —CH$_2$CH(CH$_3$)— or —CH$_2$C(CH$_3$)$_2$— can be prepared as follows:

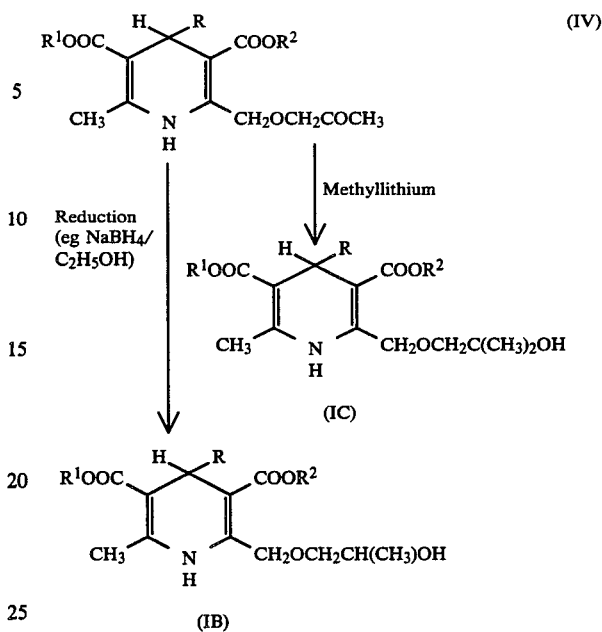

The reduction is typically carried out by reducing the ketone (IV) with a suitable reducing agent in an organic solvent, e.g. sodium borohydride in ethanol at room temperature or lithium aluminium hydride in tetrahydrofuran at about 0° C. If necessary, the reaction mixture can be heated at up to about 80° C. to accelerate the reaction. The product (IB) can then be isolated conventionally.

The reaction with methyllithium is typically carried out in an organic solvent, e.g. tetrahydrofuran, at from −80° C. to 0° C. Again the product (IC) can be isolated conventionally.

The ketones (IV) can be prepared from the acids (II). This method typically involves the reaction of the acid (II) with carbonyldiimidazole, e.g. in dichloromethane, to form the imidazolide. Reaction of this with 2,2-dimethyl-1,3-dioxan-4,6-dione in the presence of pyridine and in e.g. dichloromethane, followed by hydrolysis using e.g. aqueous acetic acid under reflux, yields the ketones.

The ketones (IV) are also active as anti-ischaemic and antihypertensive agents, and these compounds and their pharmaceutically acceptable salts form a further aspect of the invention.

(3) Compounds in which Y is —(CH$_2$)$_n$— where n is 2,3 or 4 can be prepared by the reduction of the appropriate acid of the formula:

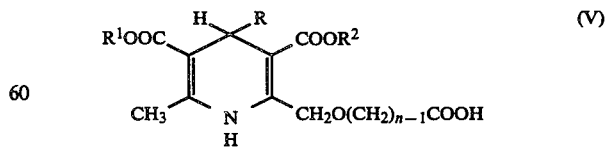

The preferred reducing agent is borane, and the reaction is typically carried out in tetrahydrofuran. Temperatures of from 0° to room temperature are usually suitable although heating at up to 60° C. can be carried out if necessary.

The starting materials (V) can be prepared by the Hantzsch synthesis [see route (1)] using the appropriately 4-substituted acetoacetate.

(4) Compounds in which Y is —$(CH_2)_n$— where n is 2, 3 or 4 can also be prepared by the reduction of the alkyl esters (VI):

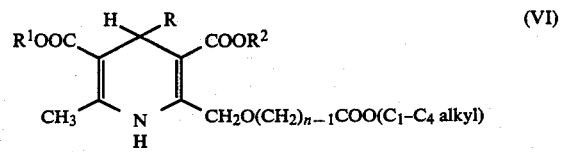

The reduction is preferably carried out using the methyl or ethyl ester, and the preferred reducing agent in this instance is lithium aluminium hydride. Typically the reaction is carried out in a suitable organic solvent, e.g. tetrahydrofuran, at from about 0° to room temperature although heating at up to 60° C. can be carried out if necessary.

Although the starting materials (VI) can, as for those of the formula (V), be prepared via the Hantzsch synthesis, when n is 4 a route is available via certain alkyne intermediates as is illustrated in detail in the Preparations hereinafter. Schematically, this route can be illustrated as follows:

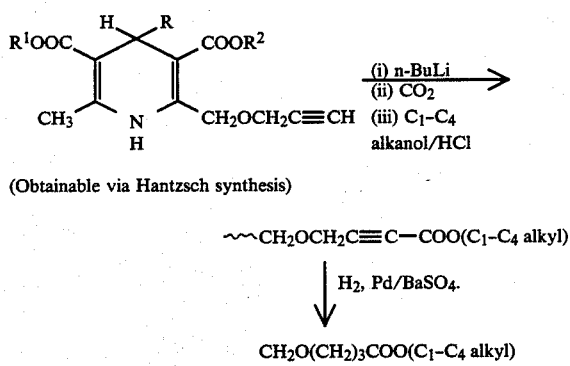

(Obtainable via Hantzsch synthesis)

Reaction of the above alkynes with mercuric ions (e.g. derived from mercuric sulphate) with aqueous mineral acid (e.g. $H_2SO_4$ in aqueous dioxane) is an alternative route to the ketones (IV). Typically the reaction is carried out with a moderate degree of heating, e.g. at 50°–70° C.

The ability of the compounds of the formulae (I) and (IV) to inhibit the movement of calcium into the cell is shown by their effectiveness in reducing the contraction of vascular tissue in vitro which is the consequence of calcium influx caused by high extracellular concentration of potassium ions. The test is performed by mounting spirally cut strips of rat aorta with one end fixed and the other attached to a force transducer. The tissue is immersed in a bath of physiological saline solution containing 2.5 mM $Ca^{2+}$ and 5.9 mM $K^\oplus$. Potassium chloride is added to the bath with a pipette to give a final $K^\oplus$ concentration of 45 millimolar. The change in tension caused by the resulting contraction of the tissue is noted. The bath is drained and replaced with fresh saline solution and, after 45 minutes, the test is repeated with the particular compound under test present in the saline solution. The concentration of compound required to reduce the response by 50% ($IC_{50}$) is recorded.

The antihypertensive activity of the compounds is evaluated after oral administration by measuring the fall in blood pressure in spontaneously hypertensive rats or renally hypertensive dogs.

For administration to man in the curative or prophylactic treatment of cardiac conditions and hypertension, oral dosages of the compounds are in the range of from 5–100 mg daily for an average adult patient (70 kg), typically 10–60 mg daily. Thus for a typical adult patient, individual tablets or capsules generally contain 5, 10 or 20 mg of active compound, in a suitable pharmaceutically acceptable vehicle or carrier. Dosages for intravenous administration are typically within the range 1 to 10 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formulae (I) and (IV) can be administered alone, but are generally administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic.

Thus in a further aspect the invention provides a pharmaceutical composition comprising a compound of the formula (I) or (IV), or a pharmaceutically acceptable salt thereof, together with a pharmaceutically acceptable diluent or carrier.

The invention also includes a compound of the formula (I) or (IV), or a pharmaceutically acceptable salt thereof, for use in medicine, in particular in the treatment of ischaemic heart disease, angina, or hypertension in a human being.

The invention also provides a method of protecting the heart from the deleterious effects of ischaemia, which comprises administering an effective amount of a compound of the formula (I) or (IV) or pharmaceutically acceptable salt thereof, or a pharmaceutical composition as defined above.

The invention also includes a method of treating hypertension which comprises administering an antihypertensive amount of a compound of the formula (I) or (IV) or pharmaceutically acceptable salt thereof, or pharmaceutical composition as defined above.

In addition to their use as pharmaceutical agents, many of the compounds of the formula (I) have been found to be useful synthetic intermediates as is described in our copending UK patent application No. 8414520 filed on 7th June, 1984. That application describes dihydropyridine anti-ischaemic and antihypertensive agents of the formula:

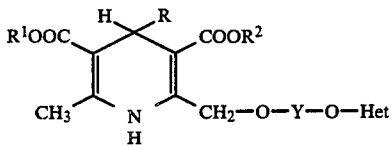

where R, R¹ and R² are as defined in the present application, Y is —(CH$_2$)$_n$— where n is 2, 3 or 4 or —CH$_2$CH(CH$_3$)—, and Het is an optionally substituted 5- or 6-membered aromatic heterocyclic group attached to the adjacent oxygen atom by a carbon atom, the heterocylic group being optionally fused to a benzene ring which is itself optionally subsititued. A typical example of "Het" is optionally substituted pyrimidinyl.

In general terms, the use of the compounds of the present application to produce the compounds of the formula (VII) can be illustrated as follows:

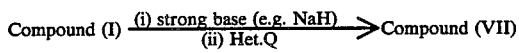

"Het" is as defined above and Q is a leaving group, preferably Cl.

The following Examples, in which all temperatures are in °C., illustrate the invention:

EXAMPLE 1

4-(2-Chlorophenyl)-3-ethoxycarbonyl-2-(2-hydroxyethoxymethyl)-5-methoxycarbonyl-6-methyl-1,4-dihydropyridine A 1M solution of borane in tetrahydrofuran (10 ml) was added dropwise over 10 minutes to a stirred, ice-cooled solution of 2-{[4-(2-chlorophenyl)-3-ethoxycarbonyl-5-methoxycarbonyl-6-methyl-1,4-dihydropyrid-2-yl]methoxy}acetic acid (2.0 g—see preparation 4 of European patent application publication No. 0100189) in tetrahydrofuran (20 ml) and the mixture was allowed to warm to room temperature. The mixture was stirred at room temperature for 3 days, quenched with water (5 ml) and evaporated. The residue was partitioned between ethyl acetate and saturated aqueous sodium hydrogen carbonate solution and the organic layer was dried over MgSO$_4$ and evaporated. The residual oil was purified by chromatography on silica gel (10 g) using hexane plus 20→50% dichloromethane followed by dichloromethane plus 0→1% methanol as eluant. Appropriate fractions were combined and evaporated and the resulting oil was crystallised from hexane to give the title compound (0.6 g), m.p. 125°–130°.

¹H-n.m.r. (CDCl$_3$, δ): 7.0–7.65 (5H, m); 5.48 (1H, s); 4.81 (2H, s); 4.12 (2H, q, J=7 Hz); 3.5–4.0 (4H, m); 3.65 (3H, s); 2.38 (3H, s) and 1.21 (3H, t, J=7 Hz).

EXAMPLE 2

4-(2,3-Dichlorophenyl)-3-ethoxycarbonyl-2-(2-hydroxyethoxymethyl)-5-methoxycarbonyl-6-methyl-1,4-dihydropyridine was prepared by the method described in Example 1 using 2-{[4-(2,3-dichlorophenyl)-3-ethoxycarbonyl-5-methoxycarbonyl-6-methyl-1,4-dihydropyrid-2-yl]methoxy}acetic acid (see Preparation 5 of European patent application publication No. 0100189) and borane as the starting materials.

The product had a m.p. of 120°–121°.

Analysis %: Found: C, 54.30; H, 5.49; N, 3.13, C$_{20}$H$_{23}$Cl$_2$NO$_6$ requires: C, 54.06; H, 5.22; N, 3.15.

EXAMPLE 3

(A).

7-(2,3-Dichlorophenyl)-8-ethoxycarbonyl-6-methoxycarbonyl-5-methyl-3-oxo-2,3,7,9-tetrahydropyrido[1,2-c]-1,4-oxazine A solution of 2-{[4-(2,3-dichlorophenyl)-3-ethoxycarbonyl-5-methoxycarbonyl-6-methyl-1,4-dihydropyrid-2-yl]methoxy}acetic acid (9.16 g), carbonyl diimidazole (3.60 g) and N-methylmorpholine (3.5 ml) in tetrahydrofuran (30 ml) was stirred at room temperature for 16 hours and then evaporated. The residue was taken up in dichloromethane and the solution washed with 2M hydrochloric acid, 10% aqueous sodium carbonate solution and water, dried over Na$_2$SO$_4$ and evaporated. Recrystallisation of the residue from ethyl acetate gave the title compound (4.70 g), m.p. 172°–173°.

Analysis %: Found: C, 53.27; H, 4.27; N, 3.15, C$_{20}$H$_{19}$Cl$_2$NO$_6$ requires: C, 53.27; H, 4.44; N, 3.27.

(B)

4-(2,3-Dichlorophenyl)-3-ethoxycarbonyl-2-(2-hydroxyethoxymethyl)-5-methoxycarbonyl-6-methyl-1,4-dihydropyridine A mixture of sodium borohydride (1.52 g) and 7-(2,3-dichlorophenyl)-8-ethoxycarbonyl-6-methoxycarbonyl-5-methyl-3-oxo-2,3,7,9-tetrahydropyrido[1,2-c]-1,4-oxazine (9.00 g) in ethanol (100 ml) was stirred at room temperature for 16 hours and then evaporated. The residue was taken up in dichloromethane and the solution was washed with water, 2M hydrochloric acid and water, dried over Na$_2$SO$_4$ and evaporated. The residue was crystallised from ether to give the title compound (6.00 g), m.p. 120°–121°. This material was confirmed spectroscopically to be identical with that obtained by the procedure of Example 2.

EXAMPLES 4 AND 5

The following compounds were prepared similarly to the procedure of the previous Example Parts (A) and (B) from corresponding starting materials:

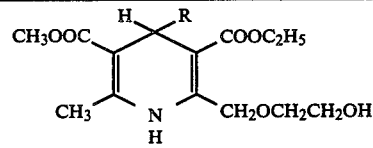

| Example No. | R | m.p. (°C.) | Analysis % (Theoretical in brackets) C | H | N |
|---|---|---|---|---|---|
| 4 | 2-Chloro-3-trifluoromethyl-phenyl | 123–4° | 52.05 (52.77 | 4.80 4.82 | 2.96 2.93) |
| 5 | 2-Chloropyrid-3-yl | 76–8° | 55.07 (55.54 | 5.77 5.60 | 6.52 6.80) |

The substituted acetic acid starting materials, namely 2-{[4-(2-chloro-3-trifluoromethylphenyl)-3-ethoxycarbonyl-5-methoxycarbonyl-6-methyl-1,4-dihydropyrid-2-yl]methoxy}acetic acid, m.p. 168°–70°, and its 4-(2-chloropyrid-3-yl) analogue, isolated as a foam, were prepared similarly to the procedure of Example 4 of European patent application publication No. 0100189. They were used directly.

EXAMPLE 6

(A)

1-{[4-(2,3-Dichlorophenyl)-3-ethoxycarbonyl-5-methoxycarbonyl-6-methyl-1,4-dihydropyrid-2-yl]methoxy}acetone A solution of carbonyl diimidazole (8.00 g) and 2-{[4-(2,3-dichlorophenyl)-3-ethoxycarbonyl-5-methoxycarbonyl-6-methyl-1,4-dihydropyrid-2-yl]methoxy}acetic acid (20.00 g) in dichloromethane (400 ml) was stirred at room temperature under nitrogen for 2 hours and then added to a solution of pyridine (3.60 g) and 2,2-dimethyl-1,3-dioxan-4,6-dione (6.50 g) in dichloromethane over 5 minutes. The mixture was stirred at room temperature for 2 days, washed successively with ice-cold 2.5M hydrochloric acid and saturated brine, dried over magnesium sulphate and evaporated. The residue was dissolved in water (300 ml) and acetic acid (150 ml) and refluxed for 5 hours. The mixture was evaporated and partitioned between diethyl ether (800 ml) and 10% aqueous sodium carbonate. The ether solution was dried over magnesium sulphate and evaporated. The residue was chromatographed on "Kieselgel 60-H" (Trade Mark) silica (50 g) using 30% hexane in dichloromethane. Fractions which contained the pure product were evaporated to give the title compound (6.5 g), m.p. 117°–119°.

Analysis %: Found: C, 55.41; H, 5.17; N, 3.46; $C_{21}H_{23}Cl_6NO_6$ requires: C, 55.27; H, 5.08; N, 3.07.

(B)

1-{[4-(2,3-Dichlorophenyl)-3-ethoxycarbonyl-5-methoxycarbonyl-6-methyl-1,4-dihydropyrid-2-yl]methoxy}propan-2-ol A solution of 1-{[4-(2,3-dichlorophenyl)-3-ethoxycarbonyl-5-methoxycarbonyl-6-methyl-1,4-dihydropyrid-2-yl]methoxy}acetone (0.46 g) and sodium borohydride (0.10 g) in ethanol (40 ml) was stirred at room temperature for 5 hours. The solution was evaporated, the residue dissolved in ethyl acetate and washed three times with water. The organic layer was dried over magnesium sulphate and evaporated. The residue was crystallized from diethyl ether/hexane to give the title compound (0.20 g), m.p. 110°–113°.

Analysis %: Found: C, 55.01; H, 5.36; N, 3.09; $C_{21}H_{25}Cl_2NO_6$ requires: C, 55.03; H, 5.50; N, 3.06.

EXAMPLE 7

1-{[4-(2,3-Dichlorophenyl)-3-ethoxycarbonyl-5-methoxycarbonyl-6-methyl-1,4-dihydropyrid-2-yl]methoxy}acetone

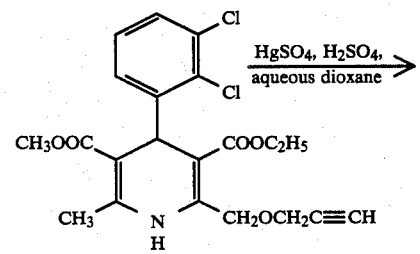

-continued

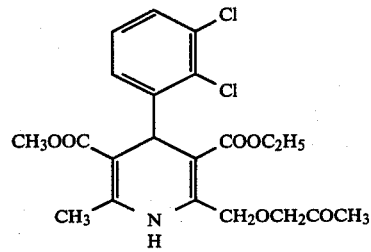

A solution of 1-{[4-(2,3-dichlorophenyl)-3-ethoxycarbonyl-5-methoxycarbonyl-6-methyl-1,4-dihydropyrid-2-yl]methoxy}-2-propyne (1.06 g), [see Preparation 3], mercuric sulphate (0.10 g) and concentrated sulphuric acid (0.2 ml) in a mixture of water (20 ml) and dioxane (20 ml) was heated at 60° for 2 hours and then evaporated. The residue was partitioned between ether and water and the organic layer washed with saturated aqueous sodium chloride solution and water, dried over sodium sulphate and evaporated to give the title compound (0.93 g), m.p. 119°–121°. This material was confirmed spectroscopically to be identical to the product of Example 6(A).

EXAMPLE 8

4-{[4-(2,3-Dichlorophenyl)-3-ethoxycarbonyl-5-methoxycarbonyl-6-methyl-1,4-dihydropyrid-2-yl]methoxy}-1-hydroxybutane

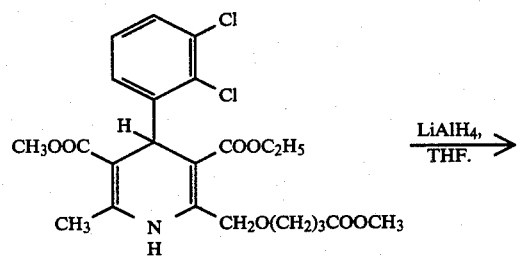

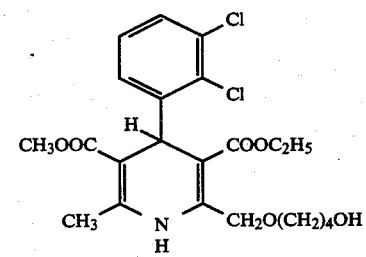

A solution of methyl 4-{[4-(2,3-dichlorophenyl)-3-ethoxycarbonyl-5-methoxycarbonyl-6-methyl-1,4-dihydropyrid-2-yl]methoxy}butanoate (0.50 g) in tetrahydrofuran (10 ml) was added dropwise over 10 minutes to a stirred, ice-cooled suspension of lithium aluminium hydride (76 mg) in tetrahydrofuran (25 ml). The mixture was stirred at 0° for 70 minutes, quenched by pouring into excess iced-water and partitioned between ethyl acetate and water. The layers were separated and the organic layer was washed twice with water, dried (MgSO$_4$) and evaporated. The residue was purified by chromatography on silica (7 g) using dichloromethane plus 0→20% v/v ethyl acetate as the eluant. Appropriate fractions were combined and evaporated and the residue was recrystallised from diisopropyl ether to give the title compound, (0.28 g), m.p. 103°–104°.

Analysis %: Found: C, 55.82; H, 5.77; N, 3.34; $C_{22}H_{27}Cl_2NO_6$ requires: C, 55.93; H, 5.72; N, 2.97.

EXAMPLE 9

1-{[4-(2,3-Dichlorophenyl)-3-ethoxycarbonyl-5-methoxycarbonyl-6-methyl-1,4-dihydropyrid-2-yl]methoxy}-2-hydroxy-2-methylpropane hemihydrate

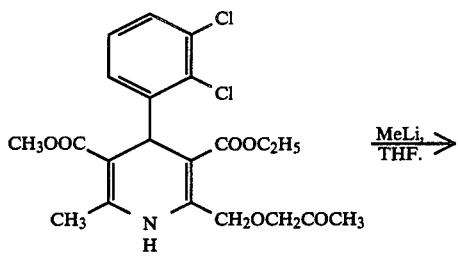

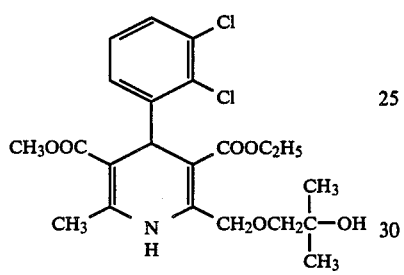

A 1.6M solution of methyllithium in ether (1.3 ml) was added dropwise over 5 minutes to a stirred solution of 1-{[4-(2,3-dichlorophenyl)-3-ethoxycarbonyl-5-methoxycarbonyl-6-methyl-1,4-dihydropyrid-2-yl]methoxy}acetone (0.46 g) (see Example 6) in tetrahydrofuran (30 ml) with cooling in an isopropanol/solid carbon dioxide bath. The mixture was stirred with cooling for 30 minutes, allowed to warm to 0° and then stirred at 0° for 20 minutes. The reaction mixture was quenched by pouring into saturated aqueous ammonium chloride solution and extracted into ethyl acetate. The organic layer was washed with water, dried over $Na_2SO_4$ and evaporated. The residue was purified by chromatography on $SiO_2$ (6 g) using toluene plus 0→50% v/v ethyl acetate as the eluant. Appropriate fractions were combined and evaporated and the residue recrystallised from diisopropyl ether to give the title compound, (0.14 g), m.p. 142°–143°.

Analysis %: Found: C, 55.14; H, 5.64; N, 2.91; $C_{22}H_{25}Cl_2NO_6.0.5H_2O$ requires: C, 55.11; H, 5.43; N, 2.92.

EXAMPLE 10

This Example illustrates the use of the product of Example 1 as a synthetic intermediate, and is the same as Example 1 of our said copending UK application No. 8414520.

4-(2-Chlorophenyl)-3-ethoxycarbonyl-5-methoxycarbonyl-6-methyl-2-[2-(2-pyrimidinyloxy)ethoxymethyl]-1,4-dihydropyridine Sodium hydride (90 mg. of an 80% by weight dispersion in oil) was added to a solution of 4-(2-chlorophenyl)-3-ethoxycarbonyl-2-(2-hydroxyethoxymethyl)-3-methoxycarbonyl-6-methyl-1,4-dihydropyridine (0.60 g) in tetrahydrofuran (20 ml) and the mixture stirred at room temperature for 45 minutes and then treated with 2-chloropyrimidine (0.17 g). The mixture was stirred at room temperature for 3 days and evaporated. The residue was dissolved in ethyl acetate and the solution washed successively with 2M hydrochloric acid, 5% aqueous sodium carbonate solution and brine, dried over $MgSO_4$ and evaporated. The residue was crystallised from ether to give the title compound (90 mg), m.p. 101°.

Analysis %: Found: C, 58.77; H, 5.52; N, 8.50; $C_{24}H_{26}ClN_3O_6$ requires: C, 59.07; H, 5.37; N, 8.61.

The following Preparations, in which all temperatures are in °C., illustrate the preparation of certain starting materials:

PREPARATION 1

Methyl 4-{[4-(2,3-dichlorophenyl)-3-ethoxycarbonyl-5-methoxycarbonyl-6-methyl-1,4-dihydropyrid-2-yl]methoxy} butanoate

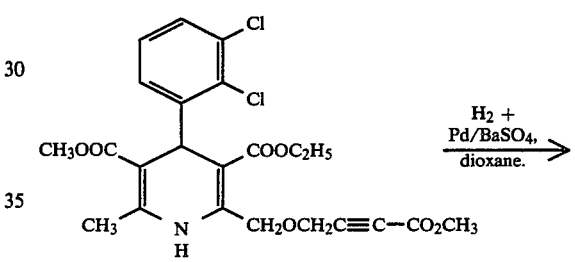

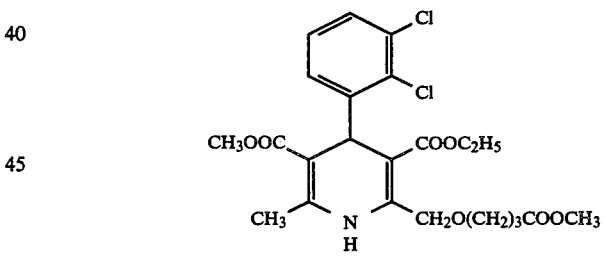

A solution of methyl 4-{[4-(2,3-dichlorophenyl)-3-ethoxycarbonyl-5-methoxycarbonyl-6-methyl-1,4-dihydropyrid-2-yl]methoxy}but-2-ynoate (1.00 g) in dioxane (30 ml) was stirred under one atmosphere (1.0333 kg.cm.$^{-2}$) of hydrogen at room temperature in the presence of 5% palladium on barium sulphate. When the uptake of hydrogen had ceased the mixture was filtered and evaporated. The residue was purified by chromatography on silica (6 g) using toluene plus 0→50% ethyl acetate as the eluant. Appropriate fractions were combined and evaporated and the residue crystallised from diisopropyl ether to give the title compound (0.40 g), m.p. 78°–80°.

Analysis %: Found: C, 55.32; H, 5.42; N, 2.80; $C_{23}H_{27}Cl_2NO_7$ requires: C, 55.42; H, 5.42; N, 2.81.

PREPARATION 2

Methyl 4-{[4-(2,3-dichlorophenyl)-3-ethoxycarbonyl-5-methoxycarbonyl-6-methyl-1,4-dihydropyrid-2-yl]methoxy}but-2-ynoate

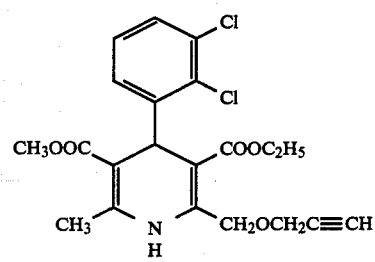

(i) n-BuLi
(ii) CO₂
(iii) MeOH/HCl

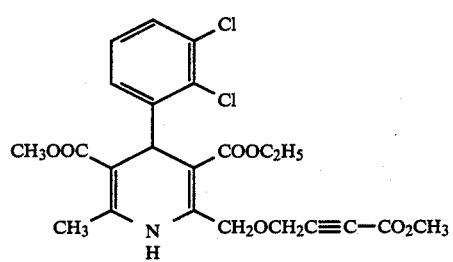

A 1.6M solution of n-butyllithium in hexane (45 ml) was added dropwise to a solution of 1-{[4-(2,3-dichlorophenyl)-3-ethoxycarbonyl-5-methoxycarbonyl-6-methyl-1,4-dihydropyrid-2-yl]methoxy}-2-propyne (132 g) in tetrahydrofuran (1 l.) keeping the temperature below −40°. The mixture was stirred at −60° for 2 hours and then carbon dioxide gas was passed through the solution for 30 minutes with cooling in an acetone/solid carbon dioxide bath. The mixture was allowed to warm to 0° while the passage of carbon dioxide gas was continued and then it was quenched with water (1 l.) and the layers separated. The aqueous layer was extracted into ether (500 ml) and the combined organic layers were washed with water, diluted with dichloromethane, washed with 1M HCl, dried over MgSO₄ and evaporated. The residue was triturated with methanol and the resulting solid collected, washed with cold (−20°) methanol and dried to give 4-{[4-(2,3-dichlorophenyl)-3-ethoxycarbonyl-5-methoxycarbonyl-6-methyl-1,4-dihydropyrid-2-yl]methoxy}but-2-ynoic acid, (83.7 g), m.p. 150°–152°.

A mixture of this crude acid (14 g) and concentrated hydrochloric acid (1 ml) in methanol (100 ml) was heated under reflux for 2 hours, concentrated to a volume of 50 ml and diluted with water (140 ml) and chloroform (140 ml). The layers were separated and the organic layer was washed with water, dried over Na₂SO₄ and evaporated. The residue was triturated with hot methanol and, after cooling, the resulting solid was collected, washed with methanol and dried to give the title ester, (9.0 g), m.p. 111°–113°.

PREPARATION 3

1-{[4-(2,3-Dichlorophenyl)-3-ethoxycarbonyl-5-methoxycarbonyl-6-methyl-1,4-dihydropyrid-2-yl]methoxy}-2-propyne

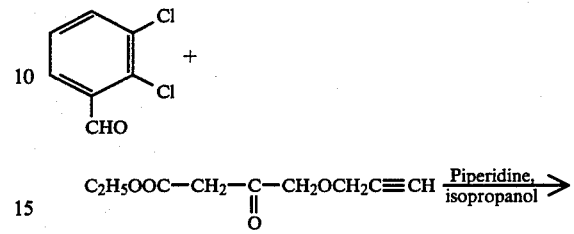

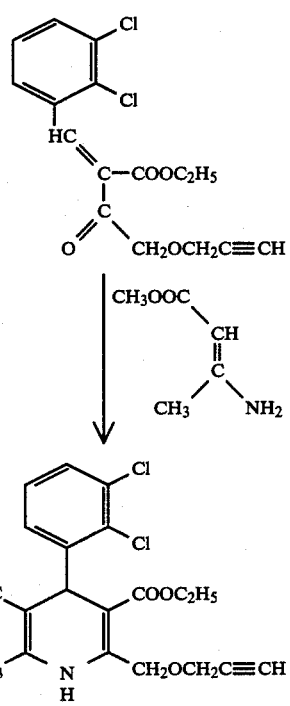

Piperidine (2.4 g) was added dropwise over 10 minutes to a stirred mixture of ethyl 4-(prop-2-ynoxy)acetoacetate (63 g) and 2,3-dichlorobenzaldehyde (60 g) in isopropanol (600 ml) and the mixture was stirred at room temperature for 24 hours. The mixture was then treated with methyl 3-aminocrotonate (39 g), stirred at room temperature for four days and evaporated. The residual oil was dissolved in methanol (300 ml) and the solution kept at −20° for two days. The resulting solid was collected, washed with cold methanol and dried to give the title compound (29.5 g), m.p. 104°–105°, which was used directly.

PREPARATION 4

Ethyl 4-(prop-2-ynoxy)acetoacetate

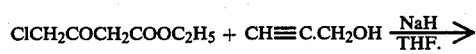

A solution of ethyl 4-chloroacetoacetate (294 g) in tetrahydrofuran (200 ml) was added over 3 hours to a stirred, ice-cooled suspension of sodium hydride (150 g of a 80% dispersion in mineral oil) in tetrahydrofuran (500 ml) at such a rate than the reaction temperature remained ≦20°. A solution of prop-2-ynol (100 g) in tetrahydrofuran (200 ml) was then added over 2 hours to the above mixture with stirring and ice-cooling at such a rate that the reaction temperature never exceeded +25°. The mixture was then stirred at room temperature for 16 hours, poured into 2M HCl (900 ml) and the layers separated. The organic layer was evaporated and the resulting red oil was separated in a separating funnel from the mineral oil. The red oil was taken up in dichloromethane and the resulting solution was washed several times with water, dried over $Na_2SO_4$ and evaporated to give the title compound (313 g) as a dark oil which was used directly in Preparation 3.

We claim:

1. A compound of the formula

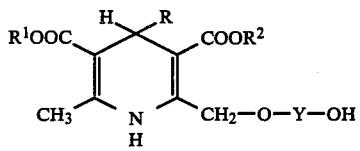

(I)

where R is selected from the group consisting of 2-chlorophenyl, 2,3-dichlorophenyl, 2-chloro-3-trifluoromethylphenyl and 2-chloropyrid-3-yl;

$R^1$ and $R^2$ are each independently $C_1$-$C_4$ alkyl or 2-methoxyethyl;

Y is $-(CH_2)_n-$, $-CH_2CH(CH_3)-$ or $-CH_2C(CH_3)_2-$; and n is 2, 3 or 4;

or a pharmaceutically acceptable salt thereof.

2. A compound according to claim 1 wherein R is 2-chlorophenyl or 2,3-dichlorophenyl.

3. A compound according to claim 2 wherein Y is $-(CH_2)_2-$, $-(CH_2)_4$, $CH_2CH(CH_3)-$ or $-CH_2C(CH_3)_2-$.

4. A compound according to claim 3 wherein $R^1$ is methyl and $R^2$ is ethyl.

5. A pharmaceutical composition comprising an anti-ischaemic or antihypertensive effective amount of a compound according to claim 1 and a pharmaceutically acceptable diluent or carrier.

6. A method of treating ischaemia in a mammal comprising the step of administering an anti-ischaemic effective amount of a compound according to claim 1.

7. A method of treating hypertension in a mammal comprising the step of administering an antihypertensive effective amount of a compound according to claim 1.

* * * * *